United States Patent [19]

Umezawa, deceased et al.

[11] Patent Number: 4,818,818

[45] Date of Patent: Apr. 4, 1989

[54] METHOD FOR THE PREPARATION OF 4'-0-TETRAHYDROPYRANYLADRIAMYCIN B

[75] Inventors: Hamao Umezawa, deceased, late of Tokyo, Japan, by Mieko Umezawa, Kazuo Umezawa, Yoji Umezawa, heirs; Tomio Takeuchi, Tokyo, Japan; Kuniaki Tatsuta, Tokyo, Japan; Yoshikazu Takahashi, Tokyo, Japan

[73] Assignee: Zaidanhojin Biseibutsu Kagaku Kenkyukai, Tokyo, Japan

[21] Appl. No.: 925,774

[22] Filed: Oct. 30, 1986

[30] Foreign Application Priority Data

Nov. 16, 1985 [JP] Japan .................... 60-257251

[51] Int. Cl.$^4$ ........................... C07H 15/24
[52] U.S. Cl. ................................ 536/6.4
[58] Field of Search ........................ 536/6.4

[56] References Cited

U.S. PATENT DOCUMENTS 4,360,664 11/1982 Umezawa et al. ................ 536/6.4

Primary Examiner—Johnnie R. Brown
Assistant Examiner—Elli Peselev
Attorney, Agent, or Firm—Frank J. Jordan; C. Bruce Hamburg; Manabu Kanesaka

[57] ABSTRACT

For the preparation of 4'-0-tetrahydropyranyladriamycin b, the 9,14-position of the starting adriamycin is previously protected with phenylboronic acid and then the 4'-position of the thus protected adriamycin is selectively tetrahydropyranylated. After the tetrahydropyranylation, the by-product of 4'-0-tetrahydropyranyladriamycin a is converted to the aimed product of 4'-0-tetrahydropyranyladriamycin b. The yield of the product of 4'-0-tetrahydropyranyladriamycin b is high.

The present invention provides a method for the preparation of 4'-0-tetrahydropyranyladriamycin b, where 3,4-dihydro-2H-pyran is added to a reaction solution containing a 9,14-protected adriamycin as obtained by (a) reacting adriamycin and phenyl-boronic acid or (b) reacting 4'-0-tetrahydropyranyladriamycin b and phenylboronic acid in the presence of an acid catalyst, for 4'-tetrahydropyranylation of the said 9,14-protected adriamycin, and then, the 9,14-protected position of the resulting product is deprotected and 4'-0-tetrahydropyranyladriamycin b is isolated by chromatography with silica-gel.

8 Claims, No Drawings

METHOD FOR THE PREPARATION OF 4'-0-TETRAHYDROPYRANYLADRIAMYCIN B

FIELD OF THE INVENTION

The present invention relates to a method for the preparation of an anthracycline-type antibiotic which is useful as a tumoricide, in particular, to that for the preparation of 4'-O-tetrahydropyranyl-adriamycin b.

BACKGROUND OF THE INVENTION

For the preparation of 4'-O-tetrahydropyranyladriamycin (hereinafter referred to as 4'-O-THPADM in short) b from adriamycin (hereinafter referred to as ADM in short, which has a structural formula (1) as given below), one method is known, as described in Japanese patent publication No. 47194/81. According to this method, ADM is directly tetrahydropyranylated (hereinafter referred to as THP-ated, in short) to obtain a mixture of 4'-O-THPADM a and b, and then the 4'-O-THPADM b is isolated therefrom by chromatography.

The 4'O-THPADM a and b as mentioned in the present invention are stereoisomers with respect to the 4'-position thereof. The absolute structure of these isomers have been determined to be (2"S)-4'-O-THPADM and (2"R)-4'-O-THPADM, respectively (Refer to "Journal of Antibiotics" by Hamao Umezawa et al., Vol. 37, pp. 1094–1097, in 1984.).

For the preparation of the 4'-O-THPADM b from daunomycin (hereinafter referred to as DM in short), two methods are known, as described in Japanese patent application OPI No. 104299/80 and No. 156300/81. (The term "OPI" as used herein means an "unexamined and published application".)

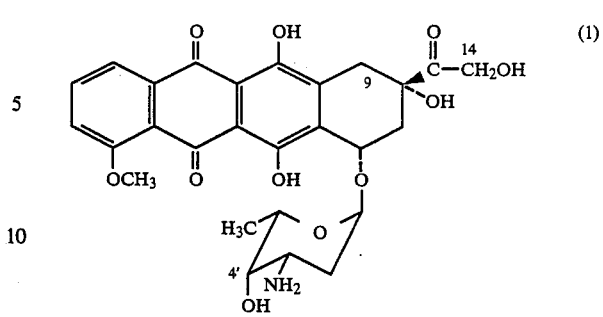

In the above-mentioned three methods, not only the desired compound or 4'-THP-ated-ADM but also by-products or 9- or 14-THP-ated compounds are formed.

The present invention is to solve this problem and to selectively THP-ate the 4'-position only. However, even if the 4'-position is selectively THP-ated, 4'-O-THPADM a which is a stereoisomer is formed as a by-product. The present invention additionally provides a method for the conversion of the 4'-O-THPADM a into the other stereoisomer of 4'-O-THPADM b, whereby the said additional problem can be also solved. Thus, the present invention provides the preparation of 4'-O-THPADM b from ADM with a high yield.

SUMMARY OF THE INVENTION

For the selective THP-ation of only the 4'-position of ADM, 9- and 14-positions of ADM are previously protected and thereafter the thus protected ADM is THP-ated.

Under the circumstances, the present inventors investigated the kind of the protecting reagents and the reaction condition thereof as well as the condition for deprotection. In addition, the THP-ation produces the mixture of 4'-O-THPADM a and b, and the desired b-isomer is isolated therefrom by chromatography, and therefore, the inventors further investigated the method for the conversion of the by-product or the a-isomer into the desired b-isomer. As a result, a reaction system as shown in the following scheme (1) has been established:

Reaction Scheme (1)

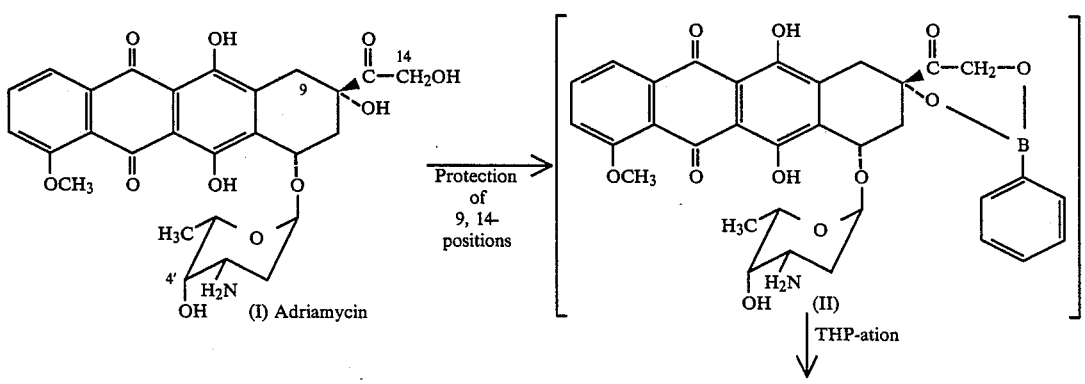

-continued
Reaction Scheme (1)

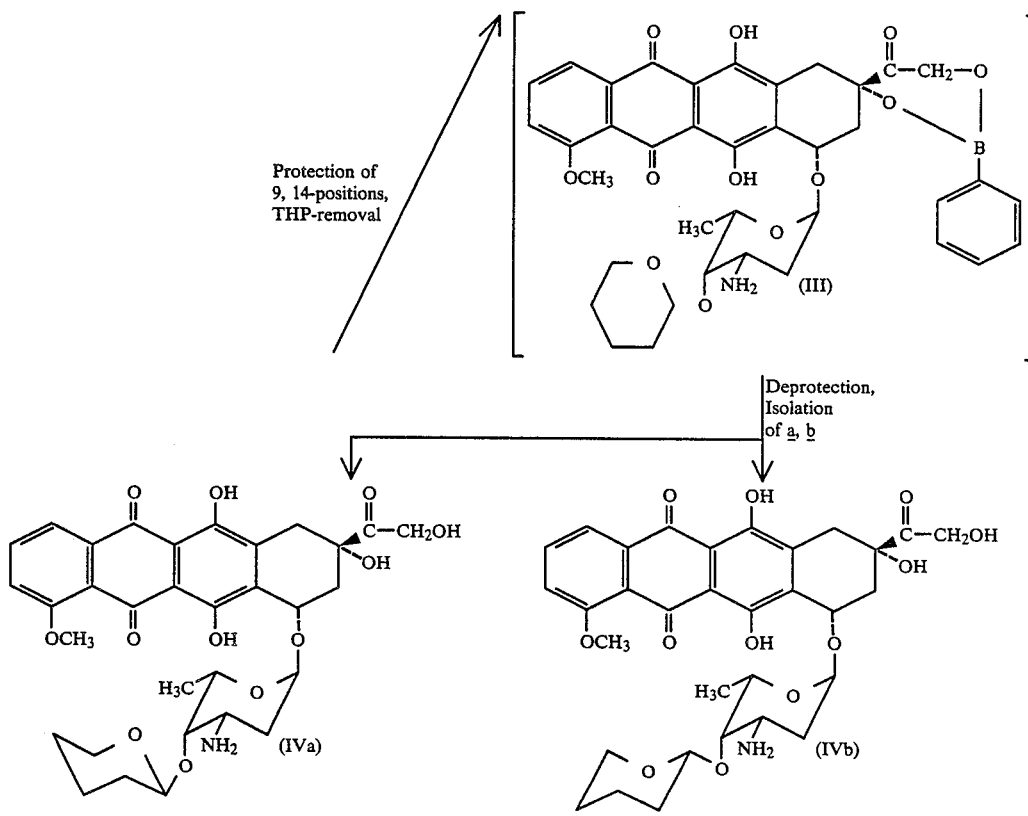

(IV a): 4'-O-tetrahydropyranyladriamycin a
(IV b): 4'-O-tetrahydropyranyladriamycin b Accordingly, the present invention provides a method for the preparation of 4'-O-THPADM b, where 3,4-dihydro-2H-pyran is added to a reaction solution containing a 9,14-protected ADM as obtained by (a) reacting ADM and phenyl-boronic acid or (b) reacting 4'-O-THPADM a and phenyl-boronic acid and an acid catalyst, for 4'-THP-ation of the said 9,14-protected ADM, and then, the 9,14-position of the resulting product is deprotected and 4'-O-THPADM b is isolated by chromatography with silica-gel.

DETAILED DESCRIPTION OF THE INVENTION

The present invention is explained in detail hereunder, by reference to the above-mentioned reaction scheme (1).

ADM to be used in the method for the present invention is used in the form of a free base or a salt such as hydrochloride thereof. The reagent for protecting the 9,14-position of the ADM to be used in the present method is phenyl boronic acid. A solvent can be used in this reaction, for example, including dimethylformamide, methylene chloride, chloroform, tetrahydrofuran, dioxane, dimethylsulfoxide or a mixture solvent thereof. The reaction temperature is preferably within the range of 0° to 50° C., and the reaction time is preferably 1 to 24 hours.

For the THP-ation of the compound of the formula (II) thus obtained, the said compound is reacted with 3,4-dihydro-2H-pyran in the presence of an acid catalyst in the solvent as used in the previous protection step, at a temperature ranging from 0° to 50° C., for 1 to 24 hours. Examples of the acid catalyst to be used in this reaction are sulfonic acids such as camphor-sulfonic acid or Lewis acids such as boron trifluoride.

The reaction solution containing the compound of the formula (III) thus obtained is washed with aqueous sodium hydrogen-carbonate solution, salt solution, water or the like and then dried to obtain a solid residue. The residue thus obtained is subjected to chromatography with a carrier of silica-gel, whereby the 9,14-protected phenyl boronic acid is removed and at the same time 4'-O-THPADM a and b are separated from each other and accordingly, the desired 4'-O-THPADM b is obtained.

Both the compounds of the formulae (II) and (III) are unstable, and these are processed in the next step without being isolated. The a-isomer as isolated from the mixture of the 4'-O-THPADM a and be is reacted with phenyl-boronic acid and an acid catalyst for the re-protection of the 9,14-position and the de-THP-ation of the 4'-position to obtain the compound of the formula (II). The solvent to be used in this reaction is a low polar solvent such as chloroform, methylene chloride or the like, since when a high polar solvent such as dimethylformamide or the like is used in the said reaction, the de-THP-ation hardly proceeds. In this step, the reaction temperature is preferably 0° to 50° C., the reaction time is preferably 1 to 24 hours, and the acid catalyst to be used is preferably a sulfonic acid compound such as camphor-sulfonic acid or a Lewis acid such as boron trifluoride.

The present invention will be explained in greater detail by reference to the following examples, which, however, are not intended to be interpreted as limiting the scope of the present invention.

EXAMPLE 1

Preparation of 4'-O-THPADM b from ADM 300 mg of adriamycin hydrochloride was dissolved in 10 ml of dimethylformamide/methylene chloride (1:1), and 125 mg of phenyl boronic acid was added thereto and stirred for 4 hours at room temperature. To this reaction solution were added 4 ml of 3,4-dihydro-2H-pyran and 48 mg of D-camphor-sulfonic acid and the whole was further stirred for 6 hours at room temperature. A mixture solution obtained by adding 20 ml of chloroform to the reaction solution was washed with a saturated sodium hydrogencarbonate-aqueous solution and a saturated salt-aqueous solution. The organic layer was dried with Glauber's salt and then concentrated and dried, and the resulting solid was subjected to silica-gel-column chromatography treatment (developer solvent: chloroform/methanol of 30/1) for isolation and re-crystallization, to finally obtain 4'-O-THPADM b. The yield of the product was 17% (55 mg). m.p. 188°–192° C. (decomposition).

EXAMPLE 2

Preparation of 4'-O-THPADM b from 4'-O-THPADM a 200 mg (0.317 mmol) of 4'-O-THPADM a free base was dissolved in 3.3 ml of methylene chloride, and then, 77 mg (0.631 mmol) of phenyl-boronic acid and 103 mg (0.443 mmol) of D-camphor-sulfonic acid were added thereto and stirred for 2 hours at room temperature. To this reaction solution were added 3.3 ml of dimethylformamide and 2.64 ml of 3,4-dihydro-2H-pyran and the whole was stirred for 4 hours. 13 ml of chloroform was added thereto and the resulting mixture solution was washed with a saturated sodium hydrogencarbonate-aqueous solution and a saturated salt-aqueous solution. The organic layer was dried with Glauber's salt and then concentrated and dried, and the resulting solid was subjected to silica-gel-column chromatography treatment (developer solvent: chloroform/methanol of 30/1) for isolation and re-crystallization, to finally obtain 4'-O-THPADM b. The yield of the product was 15% (30 mg). m.p. 188°–191° C. (decomposition).

According to the method of the present invention, 4'-O-THPADM b can be obtained with an yield of 15 to 17%. The increment of the yield is extremely remarkable over conventional methods. (For instance, the yield by the method of Japanese patent publication No. 047194/81 was 6.6%; that by the method of Japanese patent application OPI No. 104299/80 was 6.9%; and that by the method of Japanese patent application OPI No. 156300/81 was 8.7%). This merit results from the following reasons:

(1) The selective 4'-THP-ation of ADM proceeds because of the pre-protection of 9,14-position of the ADM prior to the THP-ation thereof.

(2) The phenyl-boronic acid which is the reagent for protecting the 9,14-position is stably bonded in the THP-ation or the de-THP-ation step, and this can easily be cleaved in the de-protection step.

In addition, the 4'-O-THPADM a as formed together with the formation of the product of 4'-O-THPADM b can be converted into the latter 4'-O-THPADM b in accordance with the method of the present invention. Accordingly, the product of 4'-O-THPADM b can be obtained from ADM with a high yield by the combination of the selective THP-ation of ADM and the conversion of 4'-O-THPADM a into 4'-O-THPADM b.

What is claimed is:

1. A process for the preparation of 4'-O-tetrahydropyranyladriamycin b, comprising reacting adriamycin and phenyl-boronic acid to form a 9,14-hydroxyl-protected adriamycin, reacting the thus obtained compound with 3,4-dihydro-2H-pyran for 4'-tetrahydropyranylation of the said 9,14-protected adriamycin, and then, deprotecting the 9,14-protected position of the resulting product and isolating 4'-O-tetrahydropyranyladriamycin b by chromatography with silica-gel.

2. A process for the preparation of 4'-O-tetrahydropyranyladriamycin b as claimed in claim 1, wherein the adriamycin is used in the form of a free base or a salt thereof.

3. A process for the preparation of 4'-O-tetrahydropyranyladriamycin b as claimed in claim 2, wherein said adriamycin is adriamycin hydrochloride.

4. A process for the preparation of 4'-O-tetrahydropyranyladriamycin b as claimed in claim 1, wherein the adriamycin is reacted with phenyl-boronic acid in a solvent and at a temperature of 0° C. to 50° C.

5. A process for the preparation of 4'-O-tetrahydropyranyladriamycin b as claimed in claim 1, wherein the 9,14-protected adriamycin is reacted with 3,4-dihydro-2H-pyran in the presence of an acid catalyst in the solvent at 0° to 50° C., without being isolated.

6. A process for the preparation of 4'-O-tetrahydropyranyladriamycin b as claimed in claim 1, wherein the 9,14-protected and 4'-O-tetrahydropyranylated adriamycin is subjected to chromatography with silica-gel, without being isolated, for the isolation of the product of 4'-O-tetrahydropyranyladriamycin b.

7. A process for the preparation of 4'-O-tetrahydropyranyladriamycin b, comprising reacting adriamycin and phenyl-boronic acid to form a 9,14-hydroxyl-protected adriamycin, reacting the thus obtained compound with 3,4-dihydro-2H-pyran for 4'-tetrahydropyranylation of the said 9,14-protected adriamycin, deprotecting the 9,14-protected position of the resulting product and isolating 4'-O-tetrahydropyranyladriamycin b by chromatography with silica-gel, reacting the remaining 4'-O-tetrahydropyranyl-adriamycin a with phenylboronic acid in the presence of an acid catalyst for the protection of the 9,14-position along with the 4'-detetrahydropyranylation, reacting the resulting product with 3,4-dihydro-2H-pyran for the 4'-tetrahydropyranylation of the 9,14-protected adriamycin, and then, deprotecting the 9,14-protected position of the resulting product and isolating 4'-O-tetrahydropyranyladriamycin b by chromatography with silica-gel.

8. A process for the preparation of 4'-O-tetrahydropyranyladriamycin b, comprising reacting 4'-O-tetrahydropyranyl-adriamycin a with phenyl-boronic acid in the presence of an acid catalyst for the hydroxyl-protection of the 9,14-position along with the 4'-detetrahydropyranylation, reacting the resulting product with 3,4-dihydro-2H-pyran for the 4'-tetrahydropyranylation of the 9,14-protected adriamycin, and then, deprotecting the 9,14-protected position of the resulting product and isolating 4'-O-tetrahydropyranyladriamycin b by chromatography with silica-gel.

* * * * *